US012233545B2

United States Patent
Trigui et al.

(10) Patent No.: US 12,233,545 B2
(45) Date of Patent: Feb. 25, 2025

(54) MODULAR, PROPELLED CABLE SUSPENDED ROBOT FOR INDUSTRIAL PLANTS AND UNMANNED OFFSHORE PLATFORMS

(71) Applicant: Saudi Arabian Oil Company, Dhahran (SA)

(72) Inventors: Hassane Trigui, Jeddah (SA); Ahmed Al Brahim, Thuwal (SA); Abdulwahab Halawani, Thuwal (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 443 days.

(21) Appl. No.: 17/657,269

(22) Filed: Mar. 30, 2022

(65) Prior Publication Data
US 2023/0311298 A1   Oct. 5, 2023

(51) Int. Cl.
*B25J 9/00* (2006.01)
*B25J 15/04* (2006.01)
*B25J 19/02* (2006.01)
*B25J 19/04* (2006.01)
(Continued)

(52) U.S. Cl.
CPC ......... *B25J 9/0009* (2013.01); *B25J 15/0441* (2013.01); *B25J 19/021* (2013.01); *B25J 19/04* (2013.01); *B66C 13/48* (2013.01); *B66C 21/08* (2013.01)

(58) Field of Classification Search
CPC ..... B25J 9/0009; B25J 15/0441; B66C 21/08; F16L 1/26; G01N 33/0004; A62C 35/10
See application file for complete search history.

(56) References Cited

U.S. PATENT DOCUMENTS

| 4,710,819 A | 12/1987 | Brown |
| 6,566,834 B1 | 5/2003 | Albus |
| 6,873,355 B1 | 3/2005 | Thomson et al. |

(Continued)

FOREIGN PATENT DOCUMENTS

WO    2018210632 A1    11/2018

OTHER PUBLICATIONS

Nguyen, Dinh Quan. On the study of large-dimension reconfigurable cable-driven parallel robots. Diss. Universite Montpellier 2, 2014. 161 pages.

(Continued)

*Primary Examiner* — Wade Miles
*Assistant Examiner* — Mohammed Yousef Abuelhawa
(74) *Attorney, Agent, or Firm* — Leason Ellis LLP

(57) ABSTRACT

Modular, propelled cable-driven robotic platform systems and methods of operation are disclosed. The system includes a robotic platform suspended by a system of overhead cables, motorized cable reels and pulleys. The robotic platform is configured to be equipped with tool modules for performing respective tasks. Additionally, the tool modules each have a multirotor propulsion system. A master control computer coordinates operation of the motorized cable and propulsion systems as a function of sensor data captured by navigation sensors on-board the platform so as to maneuver the robotic platform inside an industrial plant. The system is configured to maneuver around pipings and avoid obstacles in the plant in order to maximize the effective workspace that the robotic platform can reach to perform operations including inspection or repair.

17 Claims, 9 Drawing Sheets

(51) Int. Cl.
    *B66C 13/48*    (2006.01)
    *B66C 21/08*    (2006.01)

(56) References Cited

U.S. PATENT DOCUMENTS

| | | | |
|---|---|---|---|
| 7,239,106 | B2 | 7/2007 | Rodnunsky et al. |
| 8,199,197 | B2 | 6/2012 | Bennett |
| 8,666,546 | B2* | 3/2014 | Sarh .................. B25J 5/007 |
| | | | 901/1 |
| 10,369,693 | B1* | 8/2019 | Levine .................. A01C 7/085 |
| 10,471,590 | B1* | 11/2019 | Vachon .................. B25J 9/1623 |
| 10,843,340 | B2* | 11/2020 | Nguyen .................. B64F 5/10 |
| 2006/0033463 | A1 | 2/2006 | Rodnunsky |
| 2015/0314890 | A1* | 11/2015 | DesJardien ............ B25J 11/007 |
| | | | 212/324 |
| 2017/0355080 | A1* | 12/2017 | Podnar .................. B25J 19/023 |
| 2017/0369166 | A1 | 12/2017 | van den Heuvel |
| 2018/0231100 | A1 | 8/2018 | Khajepour |
| 2018/0290311 | A1* | 10/2018 | Chandra .............. B25J 15/0466 |
| 2019/0098221 | A1 | 3/2019 | Troy et al. |
| 2019/0255551 | A1* | 8/2019 | Hargadon .............. B25J 9/1664 |
| 2020/0298395 | A1 | 9/2020 | Monti |
| 2021/0003386 | A1 | 1/2021 | Caro |
| 2021/0155459 | A1 | 5/2021 | Garber |
| 2022/0024031 | A1 | 1/2022 | Trigui et al. |

OTHER PUBLICATIONS

Rasheed, Tahir, et al. "Tension distribution algorithm for planar mobile cable-driven parallel robots." Cable-Driven Parallel Robots. Springer, Cham, 2018. 268-279.

Gagliardini, Lorenzo, Marc Gouttefarde, and Séphane Caro. "Design of Reconfigurable Cable-Driven Parallel Robots." Mechatronics for Cultural Heritage and Civil Engineering. Springer, Cham, 2018. 85-113.Gagliardini, Lorenzo, Marc Gouttefarde, and Stéphane Caro. "Design of Reconfigurable Cable-Driven Parallel Robots." Mechatronics for Cultural Heritage and Civil Engineering. Springer, Cham, 2018. 85-113.

* cited by examiner

MODULAR, PROPELLED CABLE SUSPENDED ROBOT FOR INDUSTRIAL PLANTS AND UNMANNED OFFSHORE PLATFORMS

FIELD OF THE DISCLOSURE

The present invention relates to robotic devices and, in particular, a robotic platform having interchangeable tool modules fitted with propulsion systems and supported by an overhead cable and pulley suspension system for positioning the robotic platform freely inside an industrial plant to monitor, inspect, and maintain industrial structures.

BACKGROUND OF THE DISCLOSURE

Routine inspection of equipment is critical in most industries in order to ensure safety and optimize performance.

Industrial plants, such as oil and gas and petrochemicals plants, usually consist of various multiple processes that are interconnected via pipes. Most of such plants are complex and involve a massive convoluted network of pipes. Inspecting and maintaining such facilities is a complicated and rather time-consuming task especially without the aid of technology. There are multiple technologies that can enhance asset integrity and maintenance by reducing time, cost and hazards associated with these jobs. For instance, robots have been implemented to perform inspection and maintenance jobs such as ground robots, magnetic robot, robotic arms, drones, etc. However, these technologies cover specific applications and have limitations as to where they can effectively be deployed or applied.

It is with respect to these and other considerations that the disclosure made herein is presented.

SUMMARY OF THE DISCLOSURE

According to a first aspect of the disclosure, a modular, propelled cable-driven robotic platform system is disclosed. The system comprises a robotic platform including a chassis, a navigation sensor on board the chassis and an on-board controller in operative communication with the navigation sensor. The robotic platform further comprises a coupling mechanism provided on a bottom side of the chassis.

The system further comprises a cable suspension system including a plurality of cables. Each cable extends from a respective motorized cable reel through a respective elevated suspension point and is attached at a free end to the robotic platform, whereby the robotic platform is suspended from above by the cables and moveable within a three-dimensional workspace defined by a respective location of each respective elevated suspension point. Accordingly, a position of the platform within the workspace is a function of a respective length of the respective cable extending from the respective elevated suspension point to the platform.

The system further comprises a plurality of tool modules. In particular, each tool module includes a body and an equipping head on a top side of the body, the equipping head being configured to couple with the coupling mechanism of the platform, thereby equipping the platform with the tool module. The tool module further comprises a propulsion system mounted to the body. The propulsion system is configured to provide a directional thrust on the body during operation. Additionally, the tool module includes a respective tool mounted to the body for performing a respective task, and an electronic control unit. The electronic control unit is in operative communication with the propulsion system and the respective tool and configured to control operation of the propulsion system and the respective tool according to commands from a master control computer.

The system further comprises the master control computer, which includes a processor, a communication interface, a non-transitory computer-readable memory having instructions in the form of code stored therein. When executed by the processor, the instructions configure the processor to receive, via the communication interface, information captured by the navigation sensor including a present location of the platform within the workspace, and determine a location of an obstacle relative to the platform. The instructions also configure the processor to generate a navigation path suitable for moving the platform to a target location within the workspace and avoiding the obstacle. Furthermore, the instructions configure the processor to send commands for controlling the motorized reels and the propulsion system in a manner that causes the platform to move from the present location toward the target location along the navigation path. Additionally, the instructions configure the processor to, upon reaching the target location, activate the respective tool to perform the respective task at the target location.

According to a further aspect, a method for navigating a modular, propelled cable-driven robotic platform system is provided. The method comprises the step of providing, within a workspace, a modular, propelled cable-driven robotic platform system. In particular, the modular, propelled cable-driven robotic platform system comprises a robotic platform including a chassis, a navigation sensor on board the chassis and an on-board controller in operative communication with the navigation sensor. The robotic platform further comprises a coupling mechanism provided on a bottom side of the chassis.

The modular, propelled cable-driven robotic platform system further comprises a cable suspension system including a plurality of cables. Each cable extends from a respective motorized cable reel through a respective elevated suspension point and is attached at a free end to the robotic platform, whereby the robotic platform is suspended from above by the cables and moveable within a three-dimensional workspace defined by a respective location of each respective elevated suspension point. Accordingly, a position of the platform within the workspace is a function of a respective length of the respective cable extending from the respective elevated suspension point to the platform.

The modular, propelled cable-driven robotic platform system further comprises a plurality of tool modules. In particular, each tool module includes a body and an equipping head on a top side of the body, the equipping head being configured to couple with the coupling mechanism of the platform, thereby equipping the platform with the tool module. The tool module further comprises a propulsion system mounted to the body. The propulsion system is configured to provide a directional thrust on the body during operation. Additionally, the tool module includes a respective tool mounted to the body for performing a respective task, and an electronic control unit. The electronic control unit is in operative communication with the propulsion system and the respective tool and configured to control operation of the propulsion system and the respective tool according to commands from a master control computer.

The modular, propelled cable-driven robotic platform system further comprises a processor, a communication interface, a non-transitory computer-readable memory, and instructions in the form of code. When executed by the processor, the instructions configure the processor to receive, via the communication interface, information captured by the navigation sensor and, send commands for controlling the motorized reels and the propulsion system.

The method also includes the step of providing, at the processor of the master control computer, a three-dimensional (3D) model of the workspace for a cable-driven robotic platform system, the workspace being defined by the plurality of elevated cable suspension points having respective locations about the workspace. Additionally, the method includes the step of identifying, using the processor of the master control computer, based on data from one or more navigation sensors located on-board the platform, a present location of the robotic platform within the workspace. Furthermore, method includes the step of receiving, at the master control computer, a target location within the workspace for the robotic platform to be navigated to.

The method also includes the step of detecting, using master control computer, based data from one or more of the navigation sensor and the 3D model, a location within the workspace of an obstacle that obstructs a path of one or more of a cable among the plurality of cables and the robotic platform. Additionally, the method includes the step of defining, by the processor of the master control computer according to a displacement algorithm, the 3D model of the workspace, the present location, the target location and any detected obstacle locations, a navigation path.

Moreover, the method includes the step of controlling, by the processor of the master control computer, one or more motorized cable reels and the propulsion system to navigate the cable-driven robotic platform within the workspace according to the navigation path. The method also includes the step of, upon reaching the target location, activating, by the processor of the master control computer, the respective tool to perform the respective task at the target location.

These and other aspects, features, and advantages can be appreciated from the accompanying description of certain embodiments of the invention and the accompanying drawing figures and claims.

BRIEF DESCRIPTION OF THE DRAWING FIGURES

DESCRIPTION OF CERTAIN EMBODIMENTS OF THE DISCLOSURE

Figure 1:
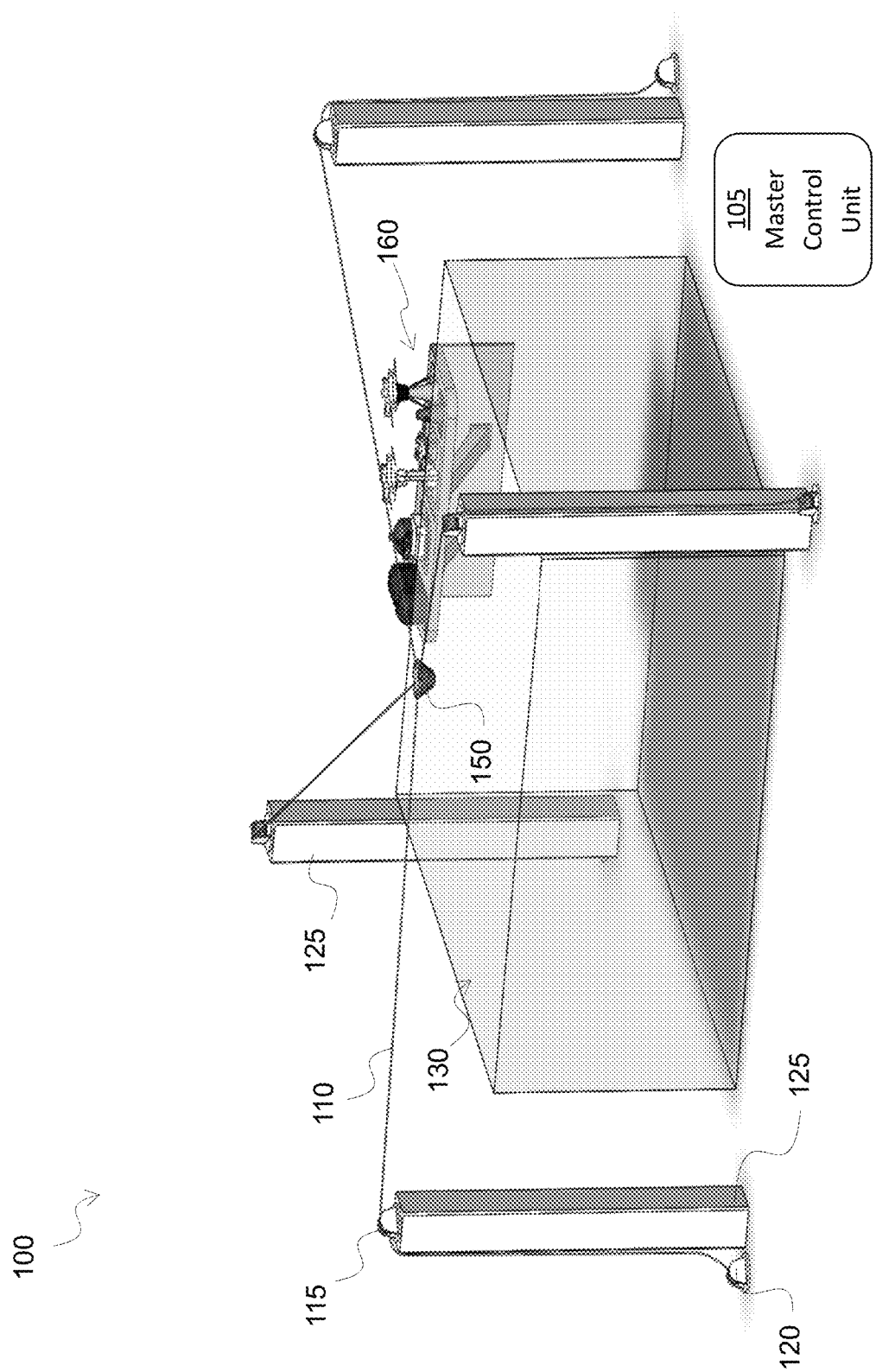
FIG. 1 is a perspective view of a modular, propelled cable-driven robotic platform system in accordance with one or more disclosed embodiments.

By way of overview and introduction, a modular, propelled cable-driven robotic platform system is disclosed. The disclosed embodiments provide a solution configured to monitor, inspect, and maintain industrial facilities using an overhead cable-driven robotic platform. The system is self-contained and modular such that the robotic platform can be selectively equipped with different tools and sensors that enable the platform to perform various types of inspections as well as execute maintenance tasks. Furthermore, according to a salient aspect, the tool modules that can be attached to the platform each include a propulsion system enabling the platform to be maneuvered within the facility using a cable suspension system or the propulsion system, or a combination of the foregoing.

Industrial plants, such as oil and gas and petrochemicals plants, usually consist of various multiple processes that are interconnected via pipes. Most of such plants are complex and involve a massive convoluted network of pipes. Inspecting and maintaining such facilities is a complicated and rather time-consuming task especially without the aid of technology. There are multiple technologies that can enhance asset integrity and maintenance by reducing time, cost and hazards associated with these jobs. For instance, robots have been implemented to perform inspection and maintenance jobs such as ground robots, magnetic robot, robotic arms, drones, etc. However, these technologies cover specific applications and have limitations as to where they can effectively be deployed or applied.

According to a salient aspect, the modular, propelled cable-driven robotic platform system is configured to reach to the majority of assets in a plant (elevated or on ground level) in order to perform various tasks in close proximity to the asset. The system, generally, includes a robotic platform that is attached to a system of overhead cables, motorized cable reels and pulleys (the "cable suspension system") which are used to move the robotic platform freely inside a plant, refinery, offshore platform, and other such industrial facilities (collectively "plants"). The cable suspension system infrastructure, namely, support columns and pulleys, is erected around the perimeter of the industrial plant such that the area of interest is reachable by the robotic platform. Embodiments of the modular, propelled cable-driven robotic platform system also are configured to maneuver around pipings and avoid obstacles in the plant in order to maximize the effective volume of the "workspace" that the robotic platform can reach to.

The platform can be equipped with any of several different tool modules that enable it to perform different tasks that include inspection, repair and maintenance, object transportation and firefighting. The tool modules are housed at a base station within the workspace where the robotic platform can be equipped and unequipped with these tools, thereby giving the platform its modularity. Each of these tools has an on-board propulsion system, such as propellers, that allow the platform to maneuver around piping and avoid obstacles in the plant, in order to maximize the volume the robotic platform can reach to. Thus it can be appreciated that the tool modules and platform is both an unmanned aerial vehicle (UAV) and cable-driven device.

In unmanned offshore platforms particularly, the modular, propelled cable-driven robotic platform system is capable of performing a majority of the inspection, monitoring, maintenance work needed to be done without human intervention. Since these unmanned platforms do not usually host humans, such a system can also be useful to detect and extinguish fires.

FIG. 1 illustrates an example cable-driven robotic platform system 100 in accordance with one or more embodiments of the disclosure. The system comprises a robotic platform 150 suspended by a set of independent overhead cables 110 which are coupled to the platform and extend to respective motorized reels 120 distributed around the plant (not shown). The overhead cables run through respective pulleys 115 which can be elevated on support columns 125 positioned around the plant. The overhead pulleys act as suspension points from where the robotic platform is suspended. Each motorized reel is configured to reel-in or feed-out a respective cable and is computer controlled by the master control unit 105.

By using the force of gravity and pulling forces of the suspended cables, the robotic platform can be mobilized freely in 3-dimensions inside a working area 130. When not operational, the robotic platform can be moved by the suspension system to a base station 160 where it can be recharged, maintained and safely protected from environmental effects. The base station 160 is also where the platform can be equipped and unequipped with various different tool modules that allow the platform to perform a variety of functions remotely.

Robotic Platform

Figure 2:
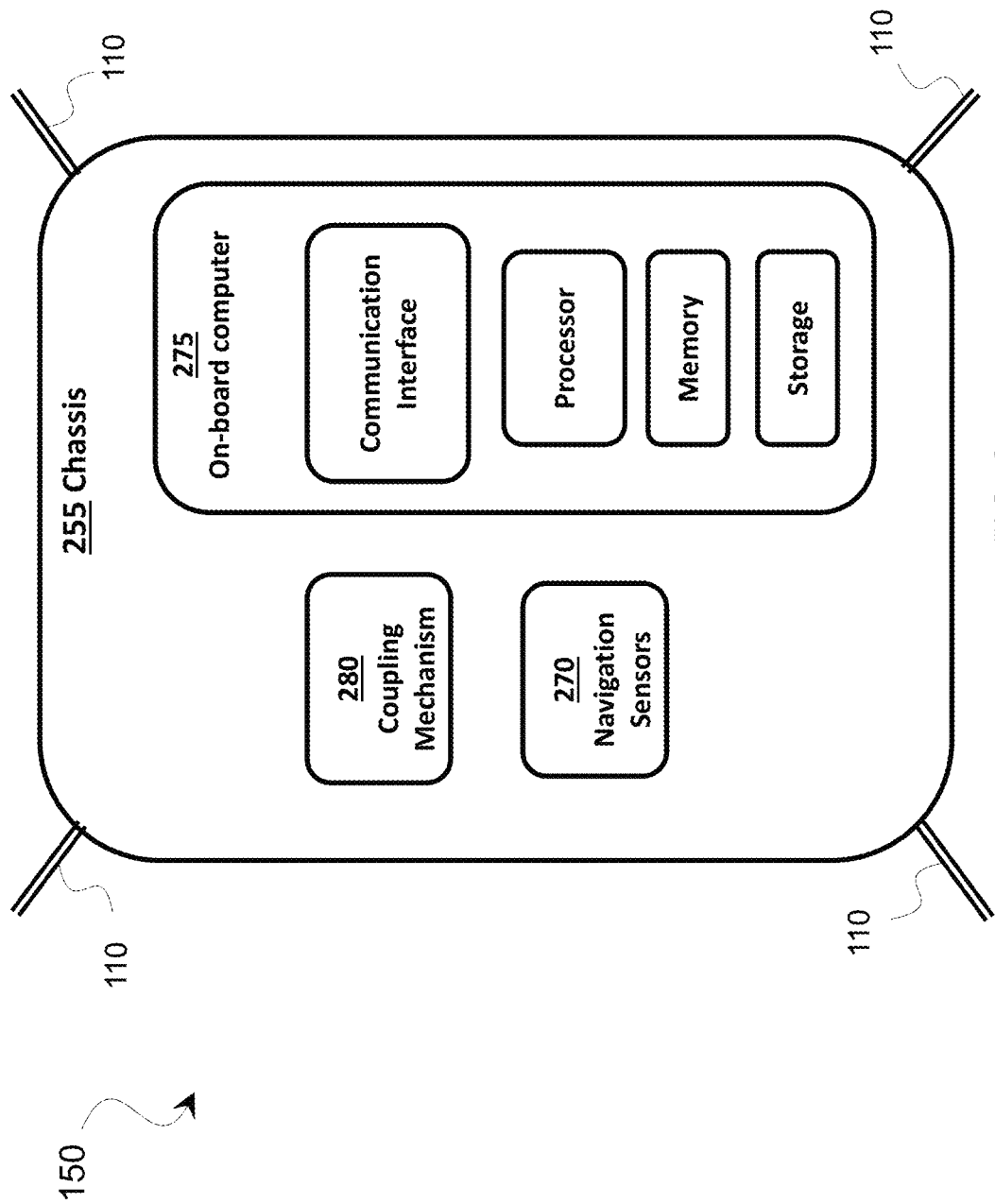
FIG. 2 is a conceptual diagram of a robotic platform system for use in the system of FIG. 1 in accordance with one or more disclosed embodiments.

FIG. 2 is a simplified conceptual diagram of the robotic platform 150 in accordance with one or more of the disclosed embodiments. The robotic platform 150 can comprise a chassis 255. The chassis is configured to be coupled to and suspended from the cables 110 and is configured to support various on-board or attached robotic, sensor and computing components that facilitate operation of the robotic platform itself as well as the modular, propelled cable-driven robotic platform system 100.

The robotic platform can be configured incorporate any number of different industrial robotic devices that are known in the art. In an embodiment, robotic platform can be connected to an external power source, for instance, power can be provided through one of the suspended cables 110. In addition, or alternatively, the robotic platform can be battery powered, in which case a battery on-board the robotic platform and/or respective tool modules (not shown) can be charged when the robotic platform is docked.

In order for the robotic platform 150 to be able to perform inspection, repair, firefighting or package transportation for unmanned rigs, the cable-driven robotic platform system is configured to be a modular system in which the chassis 255 can be equipped with interchangeable tool modules. Accordingly, the chassis can comprise a coupling mechanism 280 configured to attach the basic platform with one or more of a plurality of tool modules configured to carry a particular set of tools required for its respective application. This includes mechanisms for pick-up, release, latching, and/or docking with the different modules of the robotic platform. The coupling mechanism 280 can be operatively controlled by the on-board computer 275 and configured to couple with any of a variety of interchangeable tool modules provided on the base station 160. In an embodiment, the coupling mechanism can be configured to releasably engage with a complementary equipping head (not shown) provided on the top side of each tool module. The coupling mechanism can comprise, for example, a switchable magnet, a mechanical lock that can be actuated electrically, magnetically and/or pneumatically, among other devices that can be selectively engaged and disengaged and that are suitable for securely attaching the tool module to the robotic platform.

The robotic platform 150 can be equipped with navigation sensors 270 configured to collect information that is usable by the control computing systems to guide the movement of the robotic platform and to ensure the path of the platform is clear from any obstacles or structures within the workspace 130. In this regard, cameras and image processing, Light Detection and Ranging (LIDAR) and proximity sensors can be used as navigation sensors 270. Navigation sensors 270 such as GPS, accelerometers, and gyroscopes can also be used. Navigation sensors 270 can be provided on board the chassis of the robotic platform. In addition or alternatively, these and other sensors used in navigation can also be provided on-board the tool modules coupled to the chassis.

Subsystems of the robotic platform 150, including tool modules coupled thereto, can be interfaced to and controlled by a computer 275 mounted on-board the platform. The on-board computer can be configured to manage communication between the robotic platform and the Master Control Unit 105 (MCU) as well as communicate with each tool module, the sensors 270 and other on-board devices. The on-board computer, as would be understood, can include a processor and communication interface, among other components that are commonly found on robotic systems (e.g., computing components described in connection with FIG. 8).

As further described herein, the robotic platform 150 can be equipped with monitoring and inspection devices configured to examine plant structures in close proximity. For instance, the robotic platform can include one or more multi-DOF robotic arms configured to extend probes and sensor heads and approach structures from different angles. For example, and without limitation, following are some example known inspection device technologies that can be mounted on or coupled to the robotic platform:

Camera for visual inspection to detect cracks, external corrosion and leaks.

Thermal camera to detect any abnormalities.

Wall thickness measurements using ultrasonic, phased arrays, magnetic based sensors, eddy current or Electromagnetic-Acoustic Transducer Testing (EMAT) sensors.

Coating integrity inspection such as holiday testing and film thickness measurement devices.

Cathodic protection sensor readings.

Gas sensors can be added on-board the platform to detect for hazardous gases in the field.

Moreover, the robotic platform 150 can be equipped with one or more multi-DOF robotic arms with an end effector configured to carry and operate sensors or tools for performing repairs such as removing scales and deposits, scraping old paints, coating, spraying, welding, etc. Having the robotic arm on the platform adds another degree of flexibility to the system by reaching to complex structures or inspecting hard-to-reach areas (e.g., the 6 o'clock position of a structure). By way of further example, in some embodiments, the robotic platform can be configured to be used in firefighting by carrying water or any other substances that can be dropped at the center of a fire. Also, the robotic platform can be configured to transfer objects (e.g., packages) from one place in the working area 130 to another.

Master Control Unit

Returning now to FIG. 1, the MCU 105 is the central computing device of the system 100 and coordinates operation of the various components. It is configured to communicate with and control the motorized reels' motors and the robotic platform subsystems including any tool modules coupled to the platform. An example configuration of the computer hardware and software components of the MCU is shown and described in connection with FIG. 8.

Figure 8:
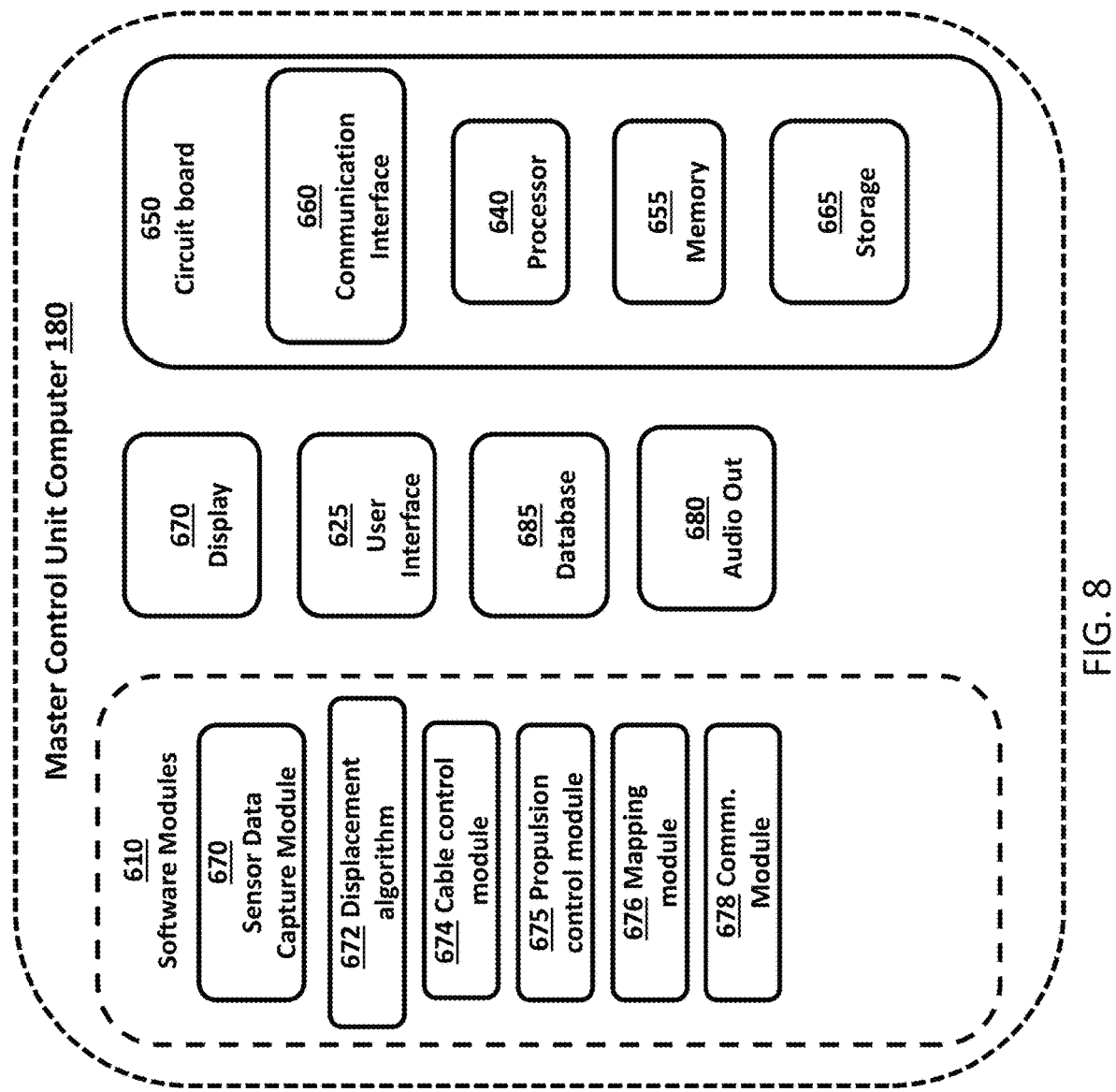
FIG. 8 is a conceptual diagram of an example control computing device platform system for use in a cable-driven robotic platform system in accordance with one or more disclosed embodiments.

As further described in relation to FIG. 8, the MCU computer comprises a processor (not shown), which executes one or more software modules in the form of machine implementable code and, in doing so, is configured to control the movement of the robotic platform within the workspace 130. More specifically, the software configures the control computer to analyze the information, as measured by navigation sensors, and geometrically calculate various dimensions of the workspace. Additionally, the software configures the MCU processor to monitor and control operational parameters of the motorized reels 120, individually, and/or the propulsion system on-board the tool modules, to controllably move the platform within the working area as a function of the navigation sensor data. Although not expressly shown in FIG. 1, it should be understood that the components of the cable-suspension system, including the motorized reel 120 motors, reels and pulleys 115 can be fitted with sensors suitable for detecting various operational parameters usable to controllably move the platform within the workspace 130. For instance, sensors provided within the reels 115 such as rotational encoders operatively coupled to the reel can detect incremental angular movements of the reel. Such sensor information can be used to determine parameters relating to how much cable has been fed out, feed rate, the length of the cable between the reel and the platform, and the like.

In some implementations, the software can also configure the processor of the MCU to evaluate inspection device measurements and operate the robotic components of the platform.

Following is a list of some of the example functions performed by the MCU:
- Receives commands through the user interface such as an instruction to move the robotic platform to a given x, y, z coordinate location within the plant.
- Controls the position and speed of the robotic platform by controlling the motors of the reels. A specific positional analysis and control algorithm can be implemented to control all the motors of the reels as the suspended cables are connected to the platform and their lengths are correlated.
- Define a site map to define the working area boundaries and define obstacles boundaries using navigation sensor 270 information and/or inspection device sensor 260 information and other site-specific parameters.
- Set a path for the robotic platform to avoid hitting obstacles.
- Use feedback sensors from robotic platform to avoid obstacles (cameras, Laser, proximity sensors, and other such navigation sensors 270).
- Perform inspection jobs, relay and store data (visual, UT, CP, etc.).
- Controls the robotic arm(s) and tools to perform a specific task.
- Turn on and control the propulsion system provided on the tool modules.
- Monitors and keep track of the system states such as communication, power, etc.
- Controls over all motions in the systems and stores data for further analysis.

Figure 3:
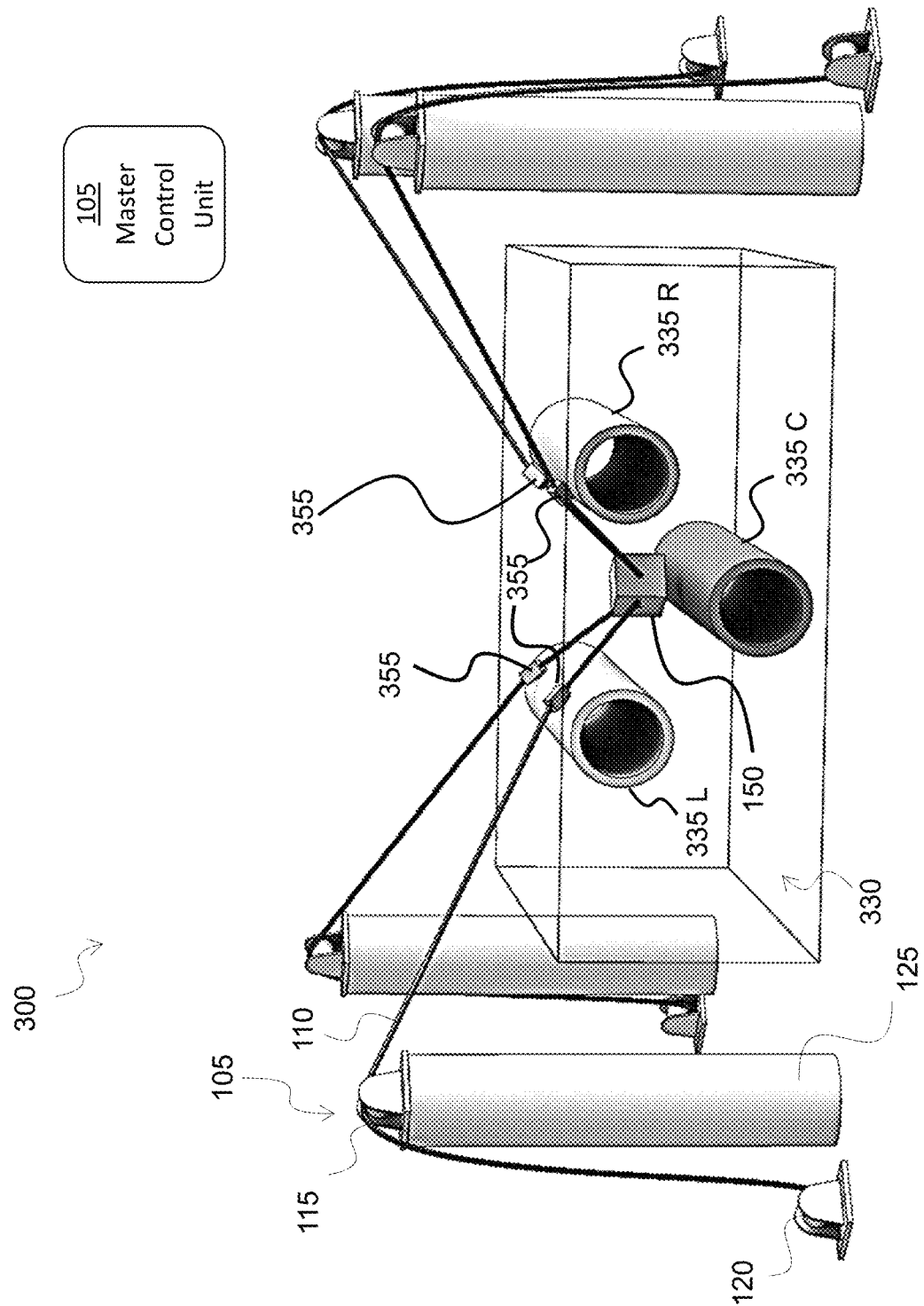
FIG. 3 is a perspective view of a modular, propelled cable-driven robotic platform system in accordance with one or more disclosed embodiments.

FIG. 3 illustrates an example cable-driven robotic platform system 300 in accordance with an embodiment of the invention. The system 300 comprises the same basic cable suspension system as the example system 100 shown in FIG. 1 and, as such, the components have like numbering in FIGS. 1 and 3. The system 300, however, further comprises "moveable wire jackets 355 that are provided on one or more of the suspended cables and that can enhance the ability of the robotic platform to be effectively mobilized within congested volumes of the workspace.

As shown, the system 300 is comprised of a robotic platform 150 suspended by a set of independent overhead cables 110 which are coupled to the platform and run all the way to respective motorized reels 120 distributed around the plant (not shown). The overhead cables run through respective pulleys 115 which can be elevated on support columns 125 positioned around the plant. The overhead pulleys act as suspension points from where the cable-driven robotic platform is suspended. Each motorized reel is configured to pull-in or feed-out a cable and is computer controlled to mobilize the robotic platform freely in 3-dimensions inside a working area 330.

In practice, the working area 330 could be a congested volume with many obstacles that might otherwise impede a robotic platform's access to structures requiring inspection or work. For example, the workspace 330 shown in FIG. 3 include structures such as the three pipes 335 L, R and C (left, right and center).

In accordance with one or more embodiments, the system 300 can include moveable cable-crawling robots 355 ("wire jackets") that are provided on one or more of the suspended cables. As shown in FIG. 3, a moveable wire jacket 355 is provided on each of the suspended cables. Wire jackets are small controllable robots that are attached firmly to respective cables and are configured to crawl in either directions along the cable between the suspension point and the platform.

According to a salient aspect, the moveable wire jackets can be controllably moved along the cables in order to change the effective locations of the suspension points and, in doing so, can create a different effective working area within which the robotic platform can be moved. Put another way, the wire jackets act as intermediate suspension points for the robotic platform in order to avoid hitting and damaging other structures that are in the way. One wire jacket or more can be used on each cable if more obstacles are to be avoided. An example configuration of a cable-driven robotic platform system having "wire jackets" is shown and described in co-pending and commonly assigned U.S. patent application Ser. No. 16/935,810, titled "CABLE SUSPENDED ROBOT FOR INDUSTRIAL PLANTS," filed Jul. 22, 2020, which is hereby incorporated by reference herein as if set forth in its entirety.

In operation, when the robotic platform is intended to be moved to a position where one (or more) of the suspended cables will hit an obstacle, a wire jacket can be dispatched, by the MCU, along the cable to the position of the obstacle. Accordingly, wire jackets can be configured to anchor on the obstacle structure. Once anchored, the wire jacket will act as a pulley or a new suspension point for the robotic platform and define a new effective workspace within which the platform can be moved.

For instance, in the example practical scenario shown in FIG. 3, in order for the robotic platform 150 to access the pipe 335C and avoid the cables hitting and scratching the pipe obstacles 335L and 335R the wire jackets 335 are moved into position and attached to pipes 335L and 335R thereby allowing the platform to be moved within the smaller effective workspace and avoid the obstacle. As further described herein, the propulsion system provided on the tool modules can further enhance the effective reach of the platform.

It is important to note that the particular location of such new suspension points are preferably accounted for in the displacement algorithm of the robotic platform since the suspended cable is no longer a single straight line, rather, multiple lines.

In addition to sensors on-board the wire jackets and robotic platform, the overall cable suspended system can be monitored by cameras fixed on top of the support columns allowing to control system or an operator to oversee the cables and wire jackets movements and ensuring the plant safety. For instance, a virtual replica of the suspended robotic platform can be digitally created on top of a 3D map of the plant. This would enable remote operators to simulate and approve all scenarios the suspended cable system can perform. In addition, it is worth noting that it is possible that some obstacles will not be able to withhold the load the wire jacket is putting along with the system weight. Accordingly, in the pre-deterministic map of a plant which is used to navigate the robotic vehicle, obstacles capable of withstanding vertical or axial force are pre-determined can be identified such that the MCU instructs the wire jackets to anchor only to identified obstacles having suitable strength.

Tool Modules

Figure 4:
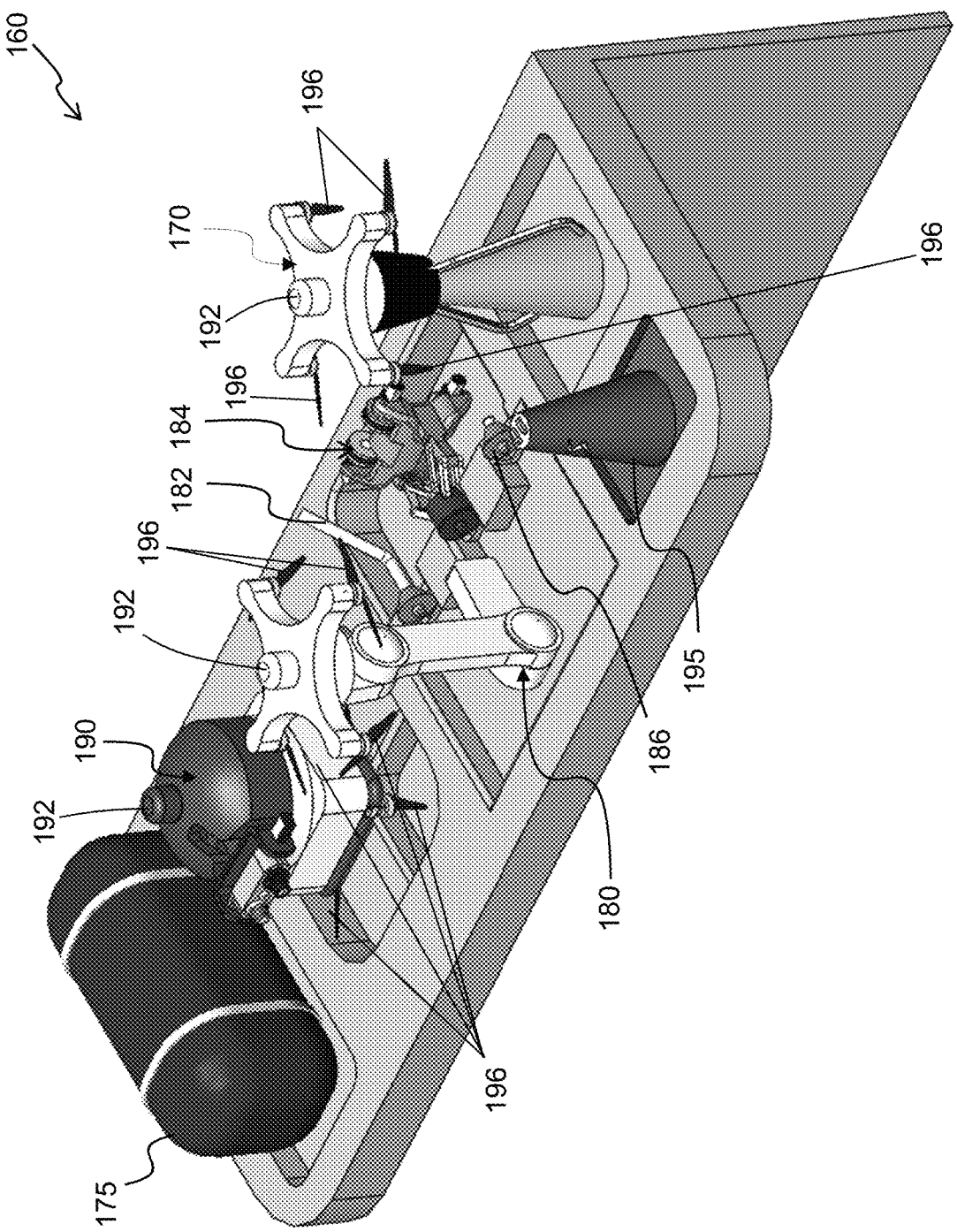
FIG. 4 is a close-up perspective view of an example configuration of a base station and tool modules of the system of FIG. 1, in accordance with one or more disclosed embodiments.

FIG. 4 is a close-up perspective view of an example configuration of the base station 160 of the system 100 shown in FIG. 1, according to an embodiment. FIG. 4 illustrates an example set of tool modules that are housed on the base station when not in use and that the robotic platform 150 can be equipped with to perform respective tasks. In an embodiment, the tool modules can include a visual inspection tool module 190, a robotic arm manipulation tool module 180 and a transportation tool module 170. Furthermore, the base station 160 can comprise a charging station 195, configured to re-charge the robotic platform 150 and other battery-powered tool modules when not in use.

As shown in FIG. 4, each of the visual inspection tool 190, robotic arm manipulation tool 180 and transportation tool 170, can comprise an equipping head 192. The equipping head 192 and the coupling mechanism 280 (not shown) provided on the robotic platform chassis are configured to engage in a manner that allows the robotic platform to pick-up each tool for use. For example, the equipping process implemented by the system 100 can include the following steps: first, the platform 150 is navigated to the position directly above the required tool module's equipping head; second, the platform is lowered until it is fully contacting the equipping head; third, the coupling mechanism and the equipping head of the tool module are coupled; fourth, the coupled platform and tool are raised to avoid hitting the other tools. As a result, the coupled platform and tool module are ready to execute their intended function.

At a minimum, the coupling mechanism 280 and equipping head 192 are configured to mechanically couple the platform 150 with the tool module. As noted, the robotic platform can be coupled with the required tool using different methods including, for example, utilizing switchable magnets that can be turned on for coupling and off for decoupling. By way of further example, the coupling mechanism can utilize a pneumatically actuated mechanical lock that will open and close by applying and releasing air pressure. In an embodiment, the coupling mechanism and equipping head can also be configured to provide an electrical connection between the platform and tool module that enables the tool module to be powered via the platform 150. In an embodiment, the coupling mechanism and equipping head can also be configured to provide a data-communications connection between the platform and tool module that enables any controllers or electronic devices on-board the tool module to be in data communication with the on-board computer 275 of the robotic platform 150 and/or the master control unit 105. In addition, or alternatively, controllers or electronic devices on-board a tool module can be in wireless communication with the on-board computer 275 and/or the master control unit 105.

In an embodiment, the transportation tool 170 comprises an electro-mechanical hook that can be actuated to grab different items in the plant, say, to pick-up and relocate items. Among the components that can be transported by this tool can include a firefighting equipment storage module 175, which can also be housed on the base station as shown in FIG. 4. For instance, in response to an alarm signal from a fire detector within the plant, the robotic platform system 100 can use the transportation tool to pick-up a firefighting equipment storage module 175 and automatically deploy its firefighting material contents (e.g., water, foam) at the location of the fire in the plant.

In an embodiment, the tool modules can include a robotic arm manipulation tool 180. As shown, the robotic arm can have multiple joints to enable the arm to articulate with multiple degrees of freedom (DOF) to contact objects that are difficult to reach. The robotic arm can also be equipped with an end effector configured to removably attach to various instrument heads. The attachment can be made using any suitable type of attachment mechanism, such as switchable magnets. For instance, as shown in FIG. 4, the instrument heads can include maintenance and repairs heads 182 for performing operations such as welding, removing scales and deposits, scraping old paints, coating, spraying and the like. The robotic arm manipulation tool 180 can also be equipped with a clamping head 184 to grasp and precisely deliver items into difficult to reach locations. As an example, this clamp could be used to deploy an inspection crawling vehicle into or on objects to obtain various measurements from them such as wall thickness measurements using ultrasonic, phased arrays, magnetic based sensors, eddy current or EMAT Coating integrity inspection such as Holiday testing and film thickness measurements, Cathodic protection and vibration readings. Such readings can also be directedly measured using a contact inspection device head 186 configured to obtain spot reading results.

In an embodiment, the instrument heads can include a firefighting hose nozzle (not shown) such that the suspended cable robotic platform can be utilized to assist during firefighting. This can be achieved by connecting the hose nozzle to the robotic arm manipulation tool 180 and a water source. The arm 180 can thus be used to spray water from above a fire in order to reach the fire zone remotely and safely without requiring any firefighters' physical intervention. The robotic manipulation arm could utilize magnetic or mechanical connections to hold the fire hose nozzle during the remote firefighting operation mode. Additionally, the robotic manipulation arm can be equipped with fire detection sensors enabling the robotic platform system to operate autonomously and track fire/heat sources. In addition or alternatively, the modular, propelled cable-driven robotic platform system 100 and arm 180 can be remotely operated manually by firefighting personnel.

Figure 5A:
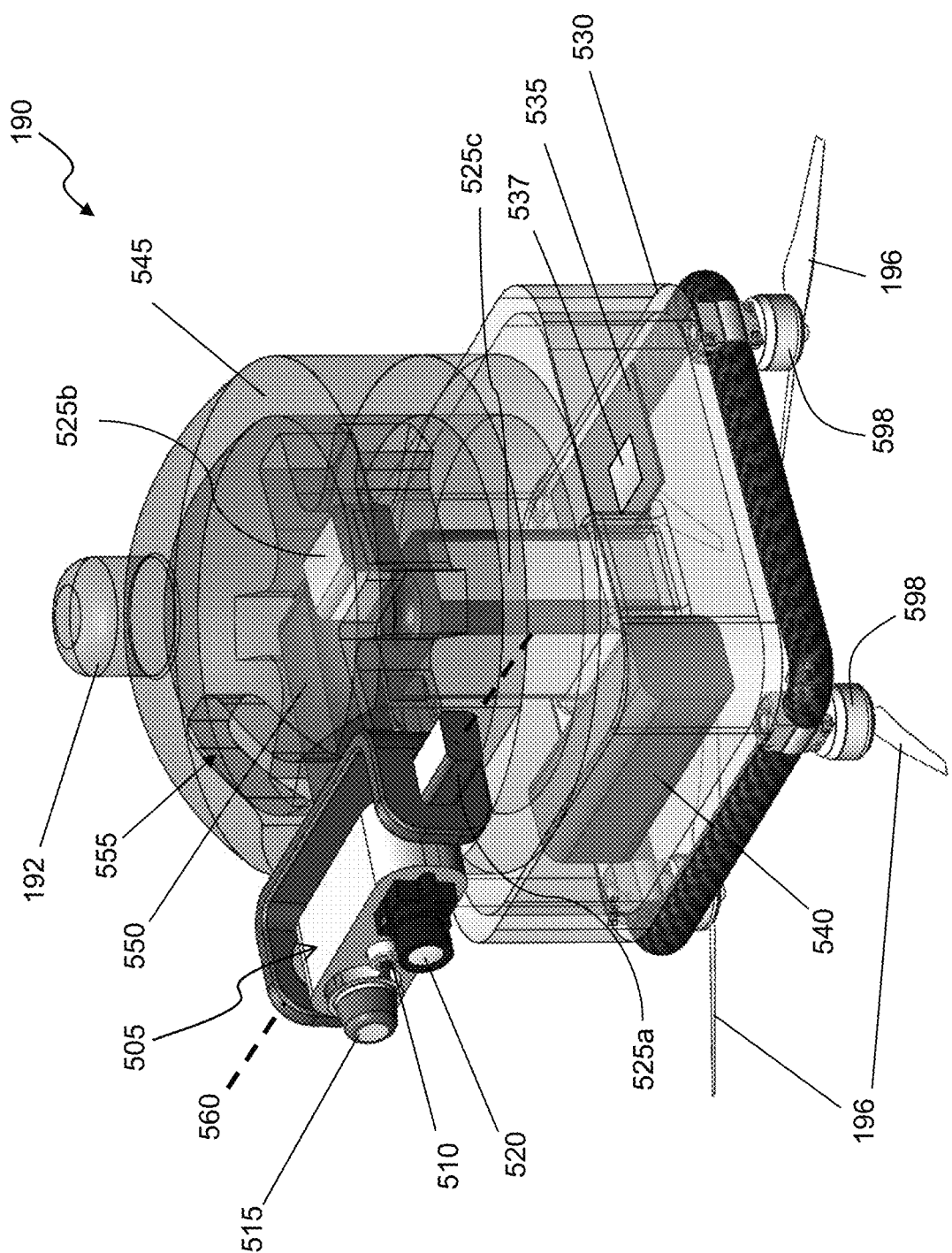
FIG. 5A-5C are each a perspective view of a visual inspection device tool module of the modular, cable-driven robotic platform system of FIG. 1 in accordance with one or more disclosed embodiments.
Figure 5C:
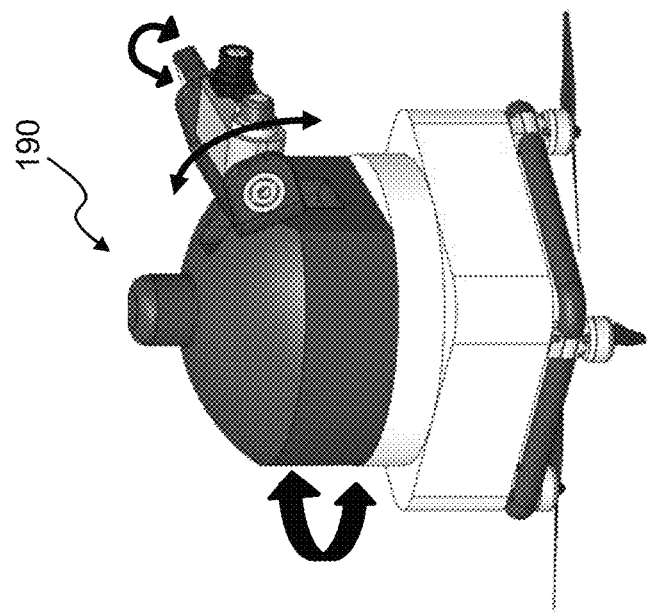
Figure 5B:
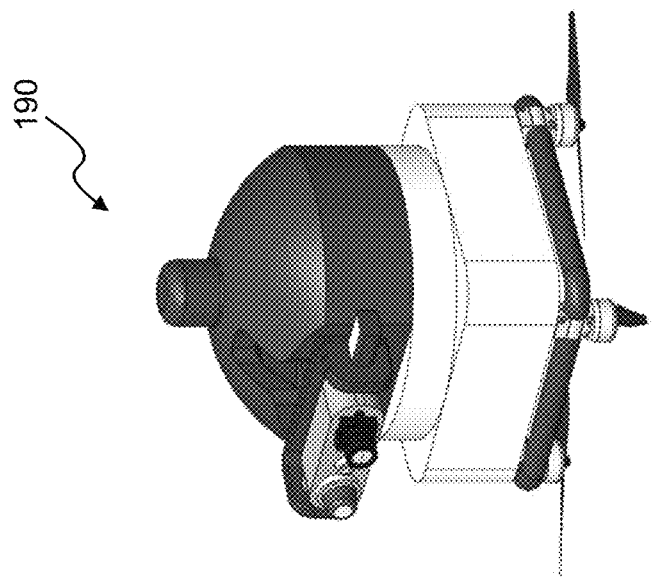

In an embodiment, the tool modules can include a visual inspection tool 190. FIG. 5A-5C further illustrate features of an example inspection tool 190 according to an embodiment. FIG. 5A illustrates an example configuration of components of the visual inspection tool 190. In FIG. 5A the inspection tool 190 is shown with transparent outer surfaces to better illustrate internal components. By comparison, FIG. 5B depicts the visual inspection tool 190 with solid outer surfaces.

As shown in FIG. 5A, the visual inspection tool, can comprise an equipping head 192. The visual inspection tool can be contactless and comprise a sensing head 505 equipped with one or more of a variety of different camera and/or sensor devices, including for example, a gas sensor and thermal camera, and visual inspection camera for detecting cracks, external corrosion and leak detection cameras. As shown in FIG. 5A, a gas sensor 510, visual camera 515 and thermal camera 520 are provided.

The enclosure of the visual inspection tool has two components, the base 530 and the dome 545. The base is fixed and houses the electronics of the visual inspection tool including a control circuit-board 535 and a battery 540. The dome 545 is configured to be rotated three hundred and sixty degrees around the vertical axis. The dome houses an arm 550 having a distal end that the sensing head 505 is pivotably mounted to. A proximal end of the arm is pivotably mounted within the dome so as to allow the arm to move up or down within a slot opening 555 provided through the dome. The sensing head 505 can be rotated about an axis 560 that extends in a horizontal direction for fine-tuning adjustments.

The visual inspection tool 190 can comprise a plurality of motors. In this example configuration, three motors 525*a-c* are provided and the number of motors matches the degrees of freedom of the imaging system. These degrees of freedom provide this tool the ability to obtain images and readings at different positions and orientations, which is vital for congested plants. In particular, motors 525*a*, 525*b* and 525*c* are configured to respectively rotate the sensing head 505, pivot the arm 550 and rotate the dome 545 about respective axes of rotation. FIG. 5C depicts the visual inspection tool 190 along with directional arrows that illustrate the degrees of freedom of rotation of the dome 545, the arm 550 and the sensing-head 505.

Propulsion System

Obstacles for the suspension cables are common in congested plant and can limit the working area accessible to the robotic platform 150, since they can prevent the platform access to areas beneath them as well as hitting the cables which effectively changes their suspension point. Thus, in order to address this challenge, each of the tool modules (i.e., the visual inspection tool 190, robotic arm manipulation tool 180 and transportation tool 170) are respectively equipped with a propulsion system. For example, as shown in FIG. 4, each tool module comprises a multirotor propulsion system comprising a plurality of propellers 196 mounted to the body of each of the tool module. The propellers can be controlled independently and are configured to provide directional thrust for the tool module and robotic platform, thereby adding to its maneuverability and increasing its reach beyond what is achieved using the cable suspension system alone. It should be understood that various types of UAV propulsion systems suitable for providing directional thrust to the tool module and robotic platform 150 can be utilized, including for example, and without limitation, propellers, rotors, impellers, turbines, and the like.

FIG. 5A further illustrates an example multirotor propulsion system of the visual inspection tool 190 according to an embodiment. It should be understood, that other tool modules can have a similarly configured propulsion and control system. As shown, four propellers 196 are mounted to the body of the visual inspection tool 190, particularly, the base 530. By way of further example, for the transportation tool module 170 and robotic arm module 180 shown in FIG. 4, the propellers 196 are mounted to arms that extend outward near the top end. It should be understood that the number and arrangement of propellers can be varied depending on application requirements.

The propellers 196 are preferably downward facing and positioned to minimize any interference with the cable suspension system. As would be understood by those in the art, the propellers can be independently driven by a respective motor 598 under the control of an electronic control unit (ECU) 537 provided on the control-board 535. The ECU can comprise a hardware microprocessor or application-specific circuit with an onboard memory unit. The control board 535 and control unit 537 is coupled to an onboard rechargeable battery 540 that provides power for the control unit as well as for the other components of the visual inspection tool 190, including the propellers 196. In some implementations, the rechargeable battery 540 can be coupled to a tethered power system (not shown) using, for example, a power transmission line extending along the suspension cables to the platform 150. The control unit 537 is configured with a flight control and navigation program module that includes software instructions for operating the propellers. Fight control and navigation can be performed according to one or more of: a pre-programmed flight plan, instructions provided from a remote computing device via a communication interface, such as the MCU 105 and/or on-board computer 275, as well as instructions from a remote operator. Accordingly, the visual inspection tool 190 can be flown manually, via remove operator control, semi-autonomously in which some of the movement and navigation of the inspection tool 190 is pre-programmed or fully autonomously using the onboard flight controller and navigation system. Flight can be controlled using the onboard flight controller alone or in combination with one or more of the MCU 105 and the computer 275 on-board the platform 150. Furthermore, flight control can be informed by data from a navigation sensor suite, which can be provided on board one or more of the visual inspection tool 190, the platform (e.g., navigation sensors 270), or any combination of the foregoing. The navigation sensor suite can include, for example, GPS, LiDAR, acoustic and optic capabilities, accelerometers and gyroscopes that provide data to the control to aid in the flight control and provide mapping functionality.

A propelled robotic platform can provide multiple advantages. Propulsion from the propellers 196 can be used to control the motion dynamics of the platform 150. It can be used to stabilize the robotic platform, especially to counteract forces on the robotic platform that are caused when performing repair or inspection activities using a tool module. Additionally, the propellers can be used to change the angle of the robotic platform (Yaw, Pitch, Roll) if a platform tilt is required to perform a certain function or reach to a confined place. Accordingly, it can be appreciated that navigation sensor suite such as GPS, accelerometers, and gyroscopes are particularly important on board such a configuration of the robotic platform.

Figure 6A:
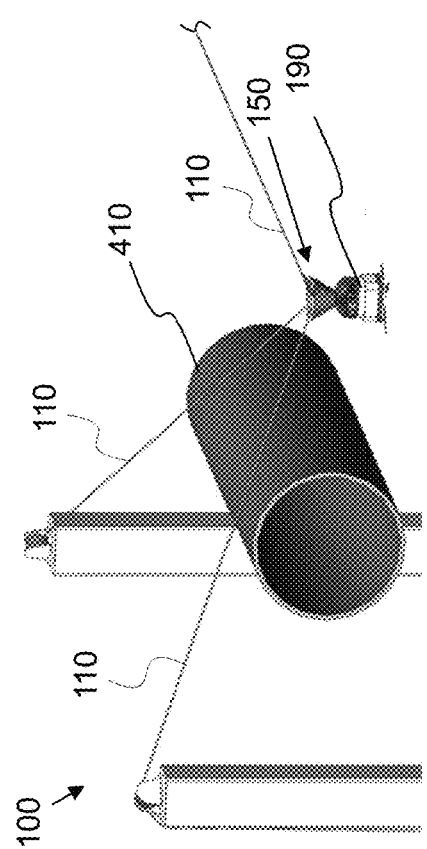
FIG. 6A is a partial perspective view of the modular, propelled cable-driven robotic platform system of FIG. 1 equipped with the visual inspection device of FIG. 5A-5C in accordance with one or more disclosed embodiments.
Figure 6C:
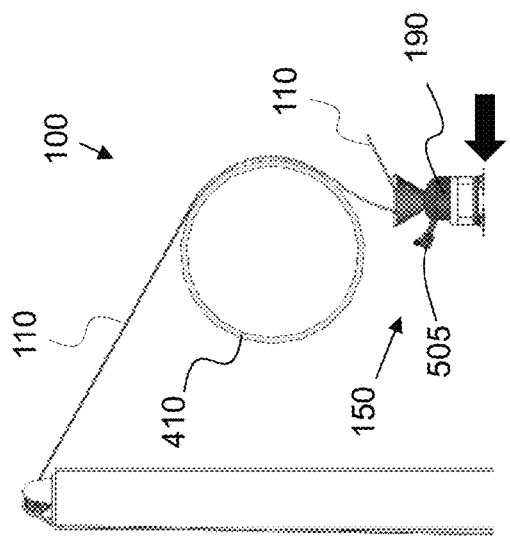
FIG. 6C is a front-view diagram of the system of FIG. 6A and showing the robotic platform maneuvered to a location relative to an obstacle using the cable-driven suspension system in accordance with one or more disclosed embodiments.
Figure 6B:
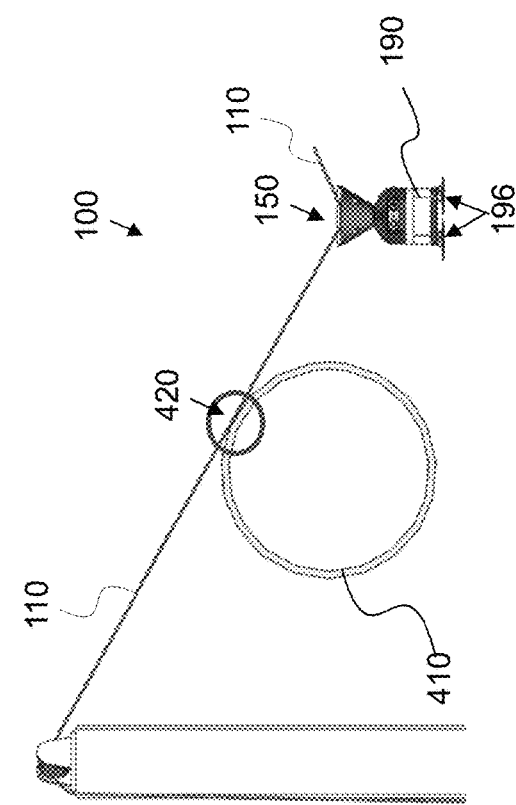
FIG. 6B is a front-view diagram of the system of FIG. 6A and showing the robotic platform maneuvered to a location relative to an obstacle using the cable-driven suspension system in accordance with one or more disclosed embodiments.

In addition to providing stabilization and adjusting rotation angle, the propulsions system further enable the robotic platform to navigate around complex structures and reach to blind spots behind and underneath obstacles. For instance, FIGS. 6A-6C illustrate an example case of using the propellers 196 mounted to the inspection device 190 to maneuver around an obstacle. More specifically, FIG. 6A is a partial perspective view of the example cable-driven robotic platform system 100 comprising a robotic platform 150 equipped with the visual inspection device 190. FIG. 6B provides a front-view of the system 100 in which the robotic platform 150 is maneuvered to a location relative to an obstacle 410 using the cable-driven suspension system. FIG. 6C provides a front-view of the system 400 in which the robotic platform 150 is maneuvered to a target location relative to an obstacle 410 using the cable-driven suspension system in combination with the propulsion system of the visual inspection tool. For example, the aim in this example scenario is to inspect the bottom surface of the pipe 410 using the visual inspection tool 190. As the platform descends, two of the cables 110 will hit the top of the pipe 410 at the circled area 420 shown in FIG. 6B, which impacts the platform suspension and its reach when depending on the cables alone for movement. Accordingly, the MCU 105 can be configured to activate the ECU 537 and to control the tool's propellers 196 to give the platform 150 an additional thrust in the direction of the arrow shown in FIG. 6C, thereby allowing the platform to position itself beneath the pipe. Moreover, using the rotational motions of visual inspection tool 190, the sensing head 505 can be positioned to face the target area of underside of the pipe for inspection.

The propulsion system, thus, allow the robotic platform 150 to translate horizontally and vertically in a confined workspace. In order to ensure precise and accurate control of the platform's trajectory, the MCU 105 can be configured to synchronize the propulsion system's motion force with adjustment of the suspension cables' 110 lengths using the motorized cable reels 120 (not shown). For instance, if the robotic platform is instructed to translate leftward, as shown in FIG. 6C, the motorized reels associated with one or more of the cables 110 can be controlled to provide enough cable slack to permit the translation.

Figure 7:
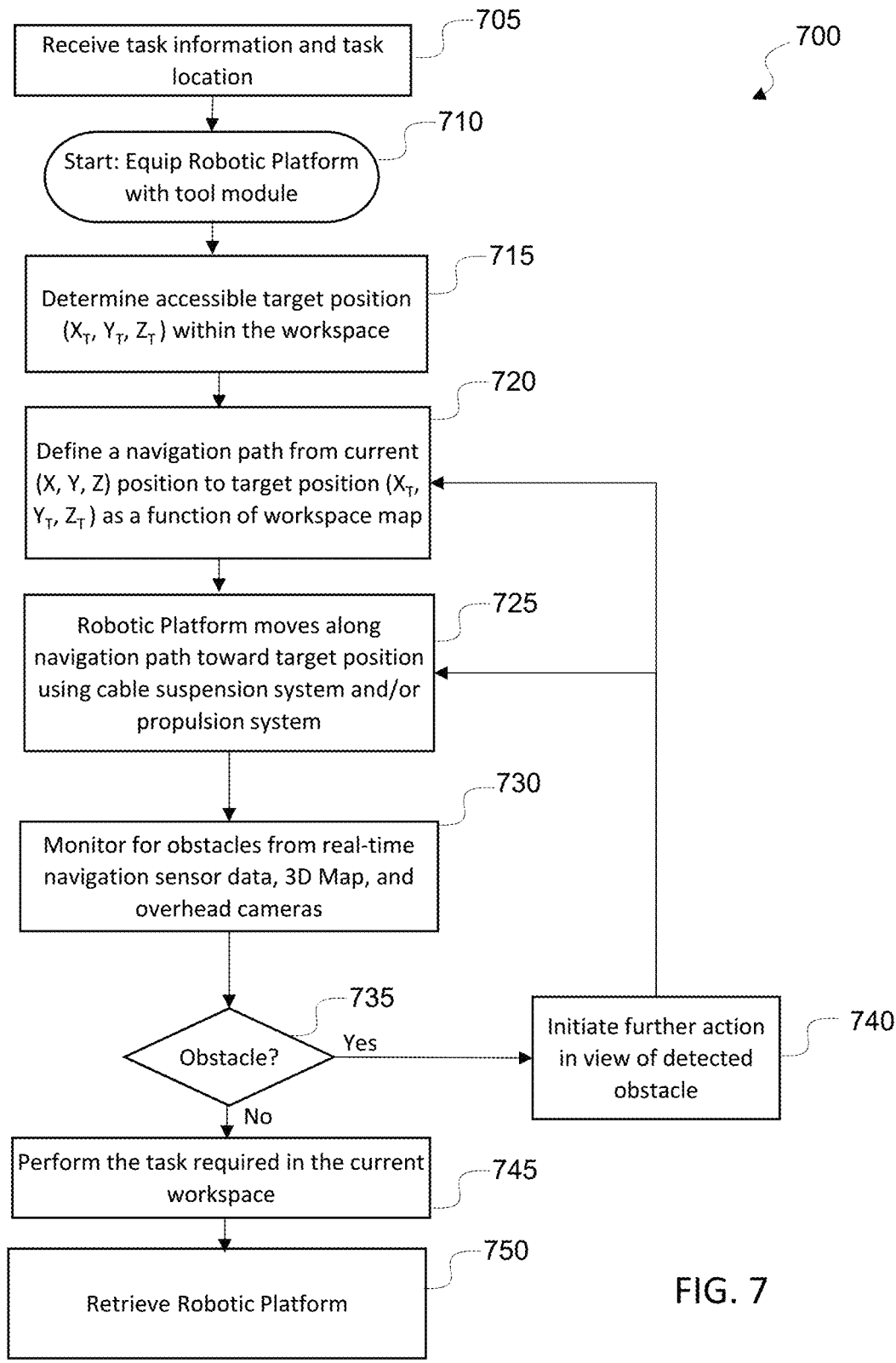
FIG. 7 is a flow diagram of an example routine for controlling a modular, propelled cable-driven robotic platform system in accordance with one or more disclosed embodiments.

FIG. 7 is a process flow diagram illustrating an example routine 700 for controllably moving a platform using a modular, propelled cable-driven robotic platform system according to principles of the disclosure. For example, and without limitation, the routine 700 is described as being performed using the system 100 shown and described in FIGS. 1-2, and 4-5C. Furthermore, the routine 700 is described in the context of the example task of inspecting the underside of a pipe 410 using the platform 150 fitted with the visual inspection tool 190, as shown in FIG. 6A-6C.

Preferably, prior to movement of the platform within a workspace, the MCU 105 is preferably provided with a well-structured and well tagged 3D map of the plant or workspace. At step 705, the MCU receives an input defining a task to be performed using a particular tool module and a location within the workspace where the task is to be performed ("task location"), for instance, the location of the underside of pipe 410 to be inspected using the inspection tool 190.

At step 710, the MCU equips the robotic platform 150 with the appropriate tool for the task, for instance, the visual inspection tool 190. Additionally, after being equipped, the platform can be moved to a starting position, say, a highest-position accessible with the cable suspension system, Z=0.

At step 715, the MCU 105 determines the target position within the workspace 330 for the platform 150 to be moved to. The target position for the platform is preferably a location that is accessible to the platform using one or more of the cable suspension system and the propulsion system, and that is sufficiently proximate to the task location to enable the visual inspection tool 190 to perform the task. The target position $(X_T, Y_T, Z_T)$ within the workspace can be, say, the position of the platform as it is shown in FIG. 6C. The accessible target position can be determined as a function of the task location, the location of one or more obstacles within the workspace, and physical constraints of the tool module, such as the range of motion of the sensing head of the visual inspection tool. In some embodiments, the target position can be received as an input, say, from a system operator.

At step 720, the MCU defines a navigation path from the platform's current (X, Y, Z) position to the target $(X_T, Y_T, Z_T)$ position. The navigation path is defined by the MCU using a displacement algorithm and according to the three-dimensional map of the workspace. Inputs to the displacement algorithm further include the current position of the platform, and the target position, and the physical constraints and movement capabilities of the cable suspension system and the propulsion system of the tool module.

In situations where the target location cannot physically be reached using only the cable suspension system, the displacement algorithm can be configured to define a navigational path having one or more waypoints that the platform is moved to using the cable-suspension system, the propulsion system, or a combination of the two. Accordingly, the navigation path can comprise one or more motion segments in which the platform is moved from one waypoint to the next using the cable-suspension system ("cable segments"), and one or more motion segments in which the platform is moved from one waypoint to the next using at least the propulsion system ("propulsion segments").

For instance, in the example shown in FIGS. 6A-6C, at step 720, the MCU can define a navigation path comprising a first cable segment in which the platform is moved from a starting position $(X, Y, Z_0)$ to an intermediate location of the platform $(X_I, Y_I, Z_I)$ shown in FIGS. 6A-6B, followed by a propulsion segment in which the platform is moved from the intermediate location $(X_I, Y_I, Z_I)$ to the target location $(X_T, Y_T, Z_T)$ shown in FIG. 6C using the propulsion system and the cable-suspension system.

At step 725, the MCU controllably moves the robotic platform according to the navigation path using one or more of the cable suspension system and the propulsion system. For instance in the example shown in FIGS. 6A-6C, the MCU can move the robotic platform, toward the intermediate waypoint $(X_I, Y_I, Z_I)$ using the cable suspension system by first controllably moving the platform to a horizontal position $(X_I, Y_I, Z_0)$ followed by controllably lowering the robotic platform vertically toward $(X_I, Y_I, Z_I)$ until either the position $(X_I, Y_I, Z_I)$ is reached or the cables 110 hit the obstacle 410. As noted, movement of the platform using the cable suspension system is performed by coordinated operation of one or more of the motorized reels 120.

During movement of the platform, at step 730, the MCU 105, in conjunction with the on-board computer 275, preferably monitors sensor data captured using one or more of the navigation sensors 270 on-board the platform 150 and/or navigation sensors on-board the tool module 190 to detect whether any obstacles are in the path of one or more of the platform and tool module or the cables. The proximity to obstacles can also be monitored by the MCU automatically from analyzing imagery captured using one or more overhead cameras. A system operator can also monitor the proximity of obstacles using the overhead camera or navigation sensor data, in addition or alternatively. Moreover, in one or more embodiments, the real-time navigation sensor data can be used to dynamically refine the workspace map and, as necessary, refine the navigation path in near real time.

As shown in FIG. 7, in the event that an obstacle is not detected at step 735, the MCU continues to move the platform toward the target position according to the navigation path until it is reached. If, however, the MCU determines that the platform or tool module or a suspended cable will hit an obstacle, at step 740, the MCU can initiate further action to avoid the obstacle and/or adapt the navigation path to the obstacle.

For example, in an embodiment, the MCU can activate the propulsion system and negotiate an obstacle using the propulsion system in order to move the platform toward the next waypoint along the navigational path.

By way of further example, in an embodiment, the MCU can dispatch one or more cable jackets to assist in avoiding the obstacle and facilitating further movement of the platform toward the next waypoint along the navigational path.

It should be understood that, in connection with taking action to avoid an obstacle at step 740, the MCU can be configured to recalibrate the effective workspace based on the position of the platform and the cables in relation to obstacles and can re-define the navigation path accordingly. Specifically, because each point of contact between a cable and an obstacle will act as a pulley or a new suspension point for the robotic platform, this location can be accounted for to re-define the effective workspace that the platform can subsequently be moved within using the cable-suspension system and/or propulsion system. The position of any new suspension points and any other effect they have on the geometry of the cable suspension system is also accounted for by the MCU in the displacement algorithm. Accordingly, prior to continuing at step 725, the method can return to repeat step 720 in view of any updated system parameters resulting from an obstacle and adaptive action.

Once the robotic platform reaches the target position ($X_T$, $Y_T$, $Z_T$), at step 745, the robotic platform performs the task required in the current workspace and as instructed by the MCU. Upon completion of the task, at step 750, the robotic platform is retrieved. For instance, retrieving the robotic platform can include retracing the navigation path in reverse order.

Throughout the process of navigating the tool-equipped platform 150 to the target position, the MCU 105 can be configured to record the navigation sensor data, as well as the control inputs provided to the cable-suspension system and propulsion system necessary to guide the platform into position and avoid any obstacles according to the navigation path. Similarly, while performing the task at the target position using the respective tool, the MCU 105 can be configured to record navigation sensor data, control inputs to the cable-suspension system, the propulsion system, and the respective tool, as well as other operational parameters of the platform and tool module (e.g., the robotic arm position, sensor head angle, dome rotation angle, platform position and orientation, and the like). This information can be recorded and used to repeat these operations using the platform and a particular tool module, or other tool module. This information can also be analyzed and used to refine the navigation path and routines for controlling the operation of the platform, the tool modules, the cable-driven suspension system and the propulsion system.

Moreover, in an embodiment, the modular, propelled cable-driven robotic platform system 100 is configured to leverage its modular tool configuration and the previously recorded and successfully traveled navigation paths to more efficiently perform a series of tasks at a target location/area using multiple different tools. For instance, when a first tool module (e.g., visual inspection tool 190) completes its respective task, the tool-equipped platform can be guided by the MCU 105 back to the base/docking station 160 by retracing the navigation path in reverse order. At the base station, the MCU can move the first tool module directly to its prescribed tool receptacle on the base station, or rest the first tool module's charging port on the charging station 195, and trigger the coupling mechanism 280 to decouple from the first tool module's equipping head 192. Thereafter the MCU can be configured to cause the robotic platform 150 to interact with another tool module by coupling once again to a second tool module. The MCU can then follow the navigation path just retraced to return to the target location and perform a second task at the worksite using the second tool module. As mentioned above, to more efficiently operate the system, the retracing of the navigation path and operation of the second tool module at the worksite can be informed by the information recorded during navigation and operation of the platform equipped with the first tool module. It should be understood that the foregoing process can be repeated to perform any number of tasks, using the various tool modules and tool configurations, at or near the worksite and other locations within the workspace.

In a further embodiment, the cable suspension system can include moveable pulleys that can be used to reconfigure (e.g., relocate) the suspension points from which the robotic platform is suspended and, hence, change the working area accessible by the robotic platform. An example configuration of a cable-driven robotic platform system having reconfigurable suspension pulleys is shown and described in co-pending and commonly assigned U.S. patent application Ser. No. 16/935,810, titled "CABLE SUSPENDED ROBOT FOR INDUSTRIAL PLANTS," filed Jul. 22, 2020, which is hereby incorporated by reference herein as if set forth in its entirety.

FIG. 8 is a block diagram illustrating an example configuration of the MCU 105 computer according to an embodiment of the present invention. As shown, the MCU can be arranged with various hardware and software components that serve to enable operation of the example cable-driven platform system configurations. It should be understood that other computing devices used in the various embodiments of the disclosure, including, the robotic platform's on-board computer 275 can have similar hardware and software components as shown and described in FIG. 8.

Components of the example MCU 105 include a processor 640 that is shown in FIG. 8 as being disposed on a circuit board 650. The circuit board can include a memory 655, a communication interface 660 and a computer readable storage medium 665 that are accessible by the processor 640.

The circuit board 650 can also include or be coupled to a power source (not shown) source for powering the computing device.

The processor 640 and/or the circuit board 650 can also be coupled to a display 670, for visually outputting information to an operator (user), a user interface 625 for receiving operator inputs, and an audio output 680 for providing audio feedback as would be understood by those in the art. As an example, the processor 640 could emit a visual signal from the display 670, for instance, a computer model depicting the dimensions of a storage container being calibrated. Although the various components are depicted either independent from, or part of the circuit board 650, it can be appreciated that the components can be arranged in various configurations.

The processor 640 serves to execute software instructions that can be loaded into the memory 655. The processor 640 can be implemented using multiple processors, a multi-processor core, or some other type of processor. The memory 655 is accessible by the processor 640, thereby enabling the processor 640 to receive and execute instructions stored on the memory 655 and/or on the computer readable storage medium 665. Memory 655 can be implemented using, for example, a random access memory (RAM) or any other suitable volatile or non-volatile computer readable storage medium. In addition, memory 655 can be fixed or removable.

The computer readable storage medium 665 can also take various forms, depending on the particular implementation. For example, the computer readable storage medium 665 can contain one or more components or devices such as a hard drive, a flash memory, a rewritable optical disk, a rewritable magnetic tape, or some combination of the above. The computer readable storage medium 665 also can be fixed or removable or remote such as cloud-based data storage systems (remote memory or storage configuration not shown). The computer readable storage medium 665, for example, can be used to maintain a database 685, which stores information relating to the capture of measurement data, the dimensional calibration of respective structures and/or data used or generated while carrying out operations and implementing aspects of the systems and methods disclosed herein.

One or more software modules 610 are encoded in the memory 655 and/or the computer readable storage medium 665. The software modules 610 can comprise one or more software programs or applications having computer program code or a set of instructions executed by the processor 640. Such computer program code or instructions for carrying out operations and implementing aspects of the systems and methods disclosed herein can be written in any combination of one or more programming languages. While the software modules 610 are stored locally in computer readable storage medium 665 or memory 655 and execute locally in the processor 640, the processor 640 can interact with a remotely-based computing platform (e.g., the robotic platform 150 computer 275) via communication interface 660, and via a local or wide area network to perform calculations, analysis, control, and/or any other operations described herein.

During execution of the software modules 610, the processor 640 is configured to perform the various operations described herein, including without limitation, the previously described routine 700 for controllably moving the platform 150. The software modules 610 can include code for implementing the aforementioned steps and other steps and actions described herein, for example and without limitation: a sensor data capture module 670, which configures the computing device 150 to capture and analyze sensor data measured using, inter alia, inspection devices (e.g., visual inspection module 190, and sensor heads 186), navigation sensors 270 and the like; a robotic platform displacement algorithm 672, which configures the processor 640 to define the navigation path and otherwise control the movement of the robotic platform 150 about the plant; a propulsion control module 675, which configures the processor to control the operation of the propulsion systems of the various tool modules; a cable control module 674, which configures the processor 640 to control the operation of the cable reels, wire-jackets and other such components of the cable suspension system; a mapping module 676, which configures the processor 640 to calculate and model the geometry of the workspace and obstacles based on the captured sensor information and other system parameters such as suspension point locations, wire-jacket positions; and a communication module 678, which configures the processor 640 to communicate with remote devices (e.g., the robotic platform 150, the motorized reels, tool modules and the like) over a communication connection such as a communication network or any wired or wireless electronic communication connection.

The program code of the software modules 610 and one or more of the non-transitory computer readable storage devices (such as the memory 655 and/or the computer readable storage medium 665) can form a computer program product that can be manufactured and/or distributed in accordance with the present disclosure.

It should be understood that various combination, alternatives and modifications of the disclosure could be devised by those skilled in the art. The disclosure is intended to embrace all such alternatives, modifications and variances that fall within the scope of the appended claims.

It is to be understood that like numerals in the drawings represent like elements through the several figures, and that not all components and/or steps described and illustrated with reference to the figures are required for all embodiments or arrangements.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

What is claimed is:

1. A modular, propelled cable-driven robotic platform system, comprising:
   a robotic platform including a chassis, a navigation sensor on board the chassis and an on-board controller in operative communication with the navigation sensor, the robotic platform further comprising a coupling mechanism provided on a bottom side of the chassis;
   a cable suspension system including:
      a plurality of cables, wherein each cable extends from a respective motorized cable reel through a respective elevated suspension point and is attached at a free end to the robotic platform, whereby the robotic platform is suspended from above by the cables and moveable within a three-dimensional workspace defined by a respective location of each respective elevated suspension point, and wherein a position of the platform within the workspace is a function of a respective length of the respective cable extending from the respective elevated suspension point to the platform;
   a plurality of tool modules, wherein the coupling mechanism is configured to releasably attach each tool module to the robotic platform and thereby support the attached tool module from the robotic platform, and each tool module including:
      a body,
      an equipping head on a top side of the body, the equipping head being configured to couple with the coupling mechanism of the platform, thereby equipping the platform with the tool module,
      a propulsion system mounted to the body, wherein the propulsion system is configured to provide a directional thrust on the body during operation, and
      a respective tool mounted to the body for performing a respective task, and
      an electronic control unit in operative communication with the propulsion system and the respective tool and configured to control operation of the propulsion system and the respective tool according to commands from a master control computer; and
   the master control computer including a processor, a communication interface, a non-transitory computer-readable memory, and instructions in the form of code that, when executed by the processor, configure the processor to:
      receive, via the communication interface, information captured by the navigation sensor including a present location of the platform within the workspace,
      determine a location of an obstacle relative to the platform,
      generate a navigation path suitable for moving the platform to a target location within the workspace avoiding the obstacle,
      send commands for controlling the motorized reels and the propulsion system in a manner that causes the platform to move from the present location toward the target location along the navigation path, and
      upon reaching the target location, activate the respective tool to perform the respective task at the target location.

2. The modular, propelled cable-driven robotic platform system of claim 1,
   wherein the propulsion system is a multirotor propulsion system comprising a plurality of propellers and a plurality of motors respectively driving the plurality of propellers.

3. The modular, propelled cable-driven robotic platform system of claim 2,
   wherein the propellers are mounted on a side of the body that is opposite the equipping head and facing in a downward direction, and wherein the propellers are independently driven using the plurality of motors.

4. The modular, propelled cable-driven robotic platform system of claim 3, the plurality of tool modules including a transportation tool module, a visual inspection tool module, and robotic arm tool module.

5. The modular, propelled cable-driven robotic platform system of claim 4, wherein the transportation tool module comprises an electro-mechanical hook as the respective tool.

6. The modular, propelled cable-driven robotic platform system of claim 4, wherein the robotic arm tool module comprises:
   a multiple degree of freedom (DOF) robotic arm mounted at a proximal end to the body, and
   an end effector provided at a distal end of the multiple DOF arm, the end effector comprising a switchable magnet attachment mechanism configured to removably attach to any one of a plurality of instrument heads.

7. The modular, propelled cable-driven robotic platform system of claim 4, wherein the visual inspection tool module comprises:
   a sensing head including one or more non-contact sensing devices;
   an enclosure comprising a base and dome, wherein the base is configured to house electronics of the visual inspection tool, the electronics including a control circuit-board and a battery, wherein the dome is rotatably mounted to the base and configured to be rotated three hundred and sixty degrees about a vertical axis, and wherein the dome comprises a slot opening through the dome;
   an arm mounted at a proximal end within the enclosure and extending through the slot toward a distal end outside of the dome, wherein the sensing head is rotatably mounted to the arm at the distal end and is rotatable about an axis that extends in a horizontal direction, and wherein the proximal end of the arm is pivotably mounted within the enclosure so as to allow the arm to move within the slot provided through the dome in a vertical direction; and
   a plurality of motors operatively connected to the control circuit-board and configured to respectively rotate the sensing head, pivot the arm, and rotate the dome under control of the control circuit-board.

8. The modular, propelled cable-driven robotic platform system of claim 7, wherein the sensing head comprises a gas sensor, a thermal camera, and a visual inspection camera.

9. The modular, propelled cable-driven robotic platform system of claim 1, further comprising:
   a base station provided within the three-dimensional workspace, wherein the base station comprises a platform having a plurality of tool receptacles configured to hold the tool modules when not in use, and a charging unit for charging a respective battery of any of the plurality of tool modules and the platform.

10. The modular, propelled cable-driven robotic platform system of claim 1, wherein the instructions further configure the processor to define a navigation path comprising a series of motion segments connecting the present location of the platform to the target location, and wherein the motion segments include at least one cable segment in which the platform is moved using the cable suspension system, and at least one propulsion segment in which the platform is moved using the cable suspension system and the propulsion system.

11. A method for navigating a modular, propelled cable-driven robotic platform system, the method comprising:
providing, within a workspace, a modular, propelled cable-driven robotic platform system comprising:
a robotic platform including a chassis, a navigation sensor on board the chassis and an on-board controller in operative communication with the navigation sensor, the robotic platform further comprising a coupling mechanism provided on a bottom side of the chassis;
a cable suspension system including, a plurality of cables, wherein each cable extends from a respective motorized cable reel through a respective elevated suspension point and is attached at a free end to the robotic platform, whereby the robotic platform is suspended from above by the cables and moveable within a three-dimensional workspace defined by a respective location of each respective elevated suspension point, and wherein a position of the platform within the workspace is a function of a respective length of the respective cable extending from the respective elevated suspension point to the platform;
a plurality of tool modules, wherein the coupling mechanism is configured to releasably attach each tool module to the robotic platform and thereby support the attached tool module from the robotic platform, and each tool module including:
a body,
an equipping head on a top side of the body, the equipping head being configured to couple with the coupling mechanism of the platform, thereby equipping the platform with the tool module,
a propulsion system mounted to the body on a side of the tool that is opposite the equipping head and configured to provide a directional thrust on the body,
a respective tool mounted to the body for performing a respective task, and
an electronic control unit in operative communication with the propulsion system and the respective tool and configured to control operation of the propulsion system and the respective tool according to commands from a master control computer;
the master control computer including a processor, a communication interface, a non-transitory computer-readable memory, and instructions in the form of code that, when executed by the processor, configure the processor to receive, via the communication interface, information captured by the navigation sensor and, send commands for controlling the motorized reels and the propulsion system;
providing, at the processor of the master control computer, a three-dimensional (3D) model of the workspace for a cable-driven robotic platform system, the workspace being defined by the plurality of elevated cable suspension points having respective locations about the workspace;
identifying, using the processor of the master control computer, based on data from one or more navigation sensors located on-board the platform, a present location of the robotic platform within the workspace;
receiving, at the master control computer, an input specifying a target location within the workspace for the robotic platform to be navigated to and at least one task to be performed at the target location;
equipping, using the processor of the master control computer, the robotic platform with a first tool module among the plurality of tool modules, wherein the first tool module has a first respective tool for performing a first respective task among the at least one task;
detecting, using master control computer, based data from one or more of the navigation sensor and the 3D model, a location within the workspace of an obstacle that obstructs a path of one or more of a cable among the plurality of cables and the robotic platform;
defining, by the processor of the master control computer according to a displacement algorithm, the 3D model of the workspace, the present location, the target location and any detected obstacle locations, a navigation path;
controlling, by the processor of the master control computer, one or more motorized cable reels and the propulsion system to navigate the cable-driven robotic platform within the workspace according to the navigation path; and
upon reaching the target location, activating, by the processor of the master control computer, the first respective tool to perform the first respective task at the target location.

12. The method of claim 11, wherein the navigation path comprises a plurality of motion segments connecting the present location of the platform to the target location, and wherein the motion segments include at least one cable segment in which the platform is moved using the cable suspension system, and at least one propulsion segment in which the platform is moved using the cable suspension system and the propulsion system.

13. The method of claim 12, further comprising:
analyzing, by the processor of the master control computer, the data from the navigation sensors in real time to monitor the present location of the platform and detect a respective location of a respective obstacle while navigating the platform within the workspace; and
in response to detecting the respective obstacle at the respective location, activating the propulsion system to navigate the platform around the obstacle according to the updated navigation path.

14. The method of claim 13, further comprising:
in response to detecting the respective obstacle at the respective location, updating, by the processor of the master control computer, the navigation path based on the respective location of the respective obstacle.

15. The method of claim 13, wherein the modular, propelled cable-driven robotic platform system further comprises a base station provided within the three-dimensional workspace, wherein the base station comprises a plurality of tool receptacles configured to hold the tool modules when not in use, and a charging unit for charging a respective battery of any of the plurality of tool modules and the platform.

16. The method of claim 15, further comprising:
upon completion of the first respective task at the target location, controlling, by the processor of the master control computer, one or more motorized cable reels and the propulsion system to navigate the cable-driven robotic platform back to a location of the base station by retracing the navigation path in reverse order.

17. The method of claim 16, further comprising:
placing, with the platform under the control of the master control unit, the first respective tool in a first tool receptacle among the plurality of tool receptacles and de-coupling the first respective tool from the platform;

causing, by the master control unit, the platform to couple to a second tool module among the plurality of tool modules, the second tool module having a second respective tool for performing a second respective task among the at least one task;

controlling, by the processor of the master control computer, one or more motorized cable reels and the propulsion system to navigate the cable-driven robotic platform back to a location of the base station by retracing the navigation path; and upon reaching the target location, activating, by the processor of the master control computer, the second respective tool to perform the second respective task at the target location.

\* \* \* \* \*